United States Patent [19]

Frankham et al.

[11] Patent Number: 5,686,034

[45] Date of Patent: Nov. 11, 1997

[54] TAMPON PRODUCTION

[75] Inventors: Stephen Andrew Frankham, Balsall Common; Angela Lindsay, Nuneaton; Andrew George Wilkes, Coventry, all of United Kingdom

[73] Assignee: Courtaulds Fibres (Holdings) Limited, London, United Kingdom

[21] Appl. No.: 577,907

[22] Filed: Dec. 4, 1995

[30] Foreign Application Priority Data

Dec. 7, 1994 [GB] United Kingdom ............... 9424612

[51] Int. Cl.⁶ ............................ D01D 5/253; D01D 5/26; D01F 2/06
[52] U.S. Cl. ........................ 264/143; 264/177.13; 264/188
[58] Field of Search ........................ 264/143, 177.13, 264/188

[56] References Cited

U.S. PATENT DOCUMENTS

| | | |
|---|---|---|
| 2,186,135 | 1/1940 | Childs . |
| 2,262,871 | 11/1941 | Whitehead . |
| 2,262,872 | 11/1941 | Whitehead . |
| 4,568,506 | 2/1986 | Kiriyama et al. . |
| 5,234,645 | 8/1993 | Grindstaff . |
| 5,308,564 | 5/1994 | Grindstaff . |
| 5,443,776 | 8/1995 | Bartholomew et al. ............. 264/168 |
| 5,458,835 | 10/1995 | Wilkes et al. ....................... 264/143 |

FOREIGN PATENT DOCUMENTS

| | | |
|---|---|---|
| 86631 | 8/1983 | European Pat. Off. . |
| 301874 | 2/1989 | European Pat. Off. . |
| 655606 | 4/1929 | France . |
| 828686 | 5/1938 | France . |
| 701836 | 1/1941 | Germany . |
| 500886 | 2/1939 | United Kingdom . |
| 910864 | 11/1962 | United Kingdom . |

Primary Examiner—Leo B. Tentoni
Attorney, Agent, or Firm—Howson and Howson

[57] ABSTRACT

A method for the production of a tampon formed of a blend of regenerated solid cellulosic viscose fibres, is provided in which the blend includes a first set of fibres having a first cross-sectional characteristic and a second set of fibres having a second cross-sectional characteristic. The first cross-sectional characteristic is different from the second cross-sectional characteristic. The method includes the improvement of forming the blend by forming a tow of viscose rayon fibres having the same blend ratio of first and second sets of fibres as is required in the tampon by spinning viscose dope through a jet to form a plurality of filaments. The jet has a plurality of dimensionally controlled holes pierced therein. In this way a plurality of different fibre cross-sectional shapes or sizes are simultaneously formed directly in the tow by spinning the viscose dope through the jet having the required plurality of different shaped or sized holes pierced therein.

13 Claims, 2 Drawing Sheets

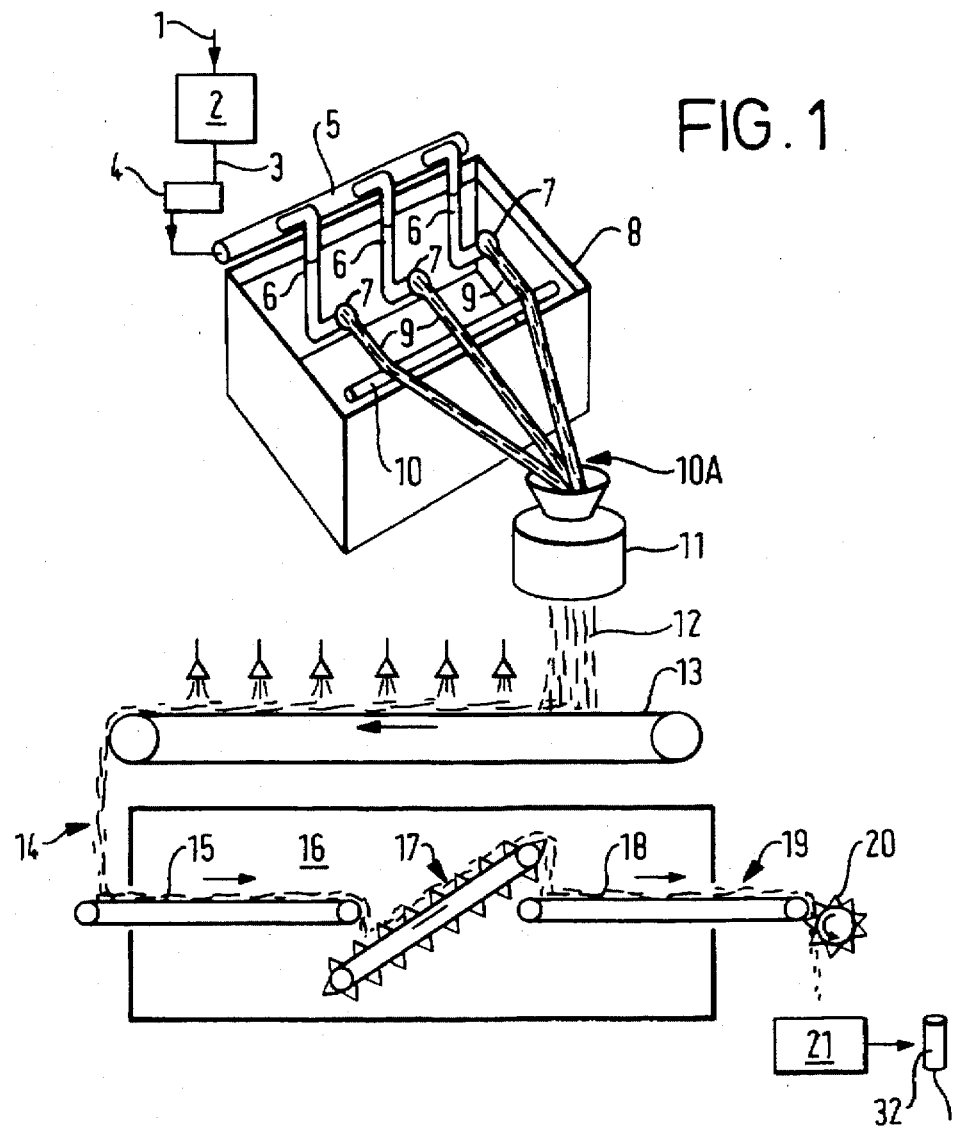
FIG. 1
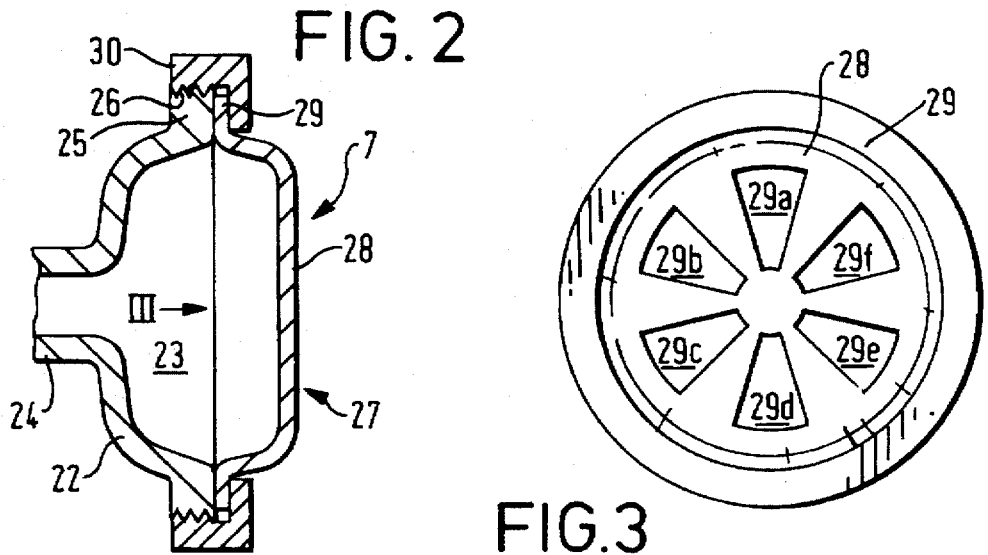
FIG. 2
FIG. 3

TAMPON PRODUCTION

BACKGROUND OF THE INVENTION

1. Field of the Invention

The present invention relates to tampons formed of fibres and has particular reference to tampons formed of blends of viscose fibres.

2. Description of the Related Art

In EP-B-0301874, the contents of which are incorporated herein by way of reference, there is described a method of manufacturing shaped viscose fibres which have particular use in the production of absorbent products, particularly tampons. In a preferred form of the invention described in EP-B-0301874 Y-shaped cross-sectional fibres are produced by the spinning of conventional viscose dope into a conventional spin bath so as to form shaped fibres of a specified decitex and specified geometrical cross-sectional shape.

These shaped fibres have enhanced absorbency characteristics compared to conventional viscose fibres, which, even though spun through circular spinnerette holes, tend to have an irregular cross-sectional shape. If a fibre product is required which needs to have an absorbency intermediate between that of the shaped fibres and conventional fibres, it is possible to blend the irregular and shaped fibres together. Blending is, of course, a well known technique in the fibre industry. Conventionally, bales of different fibre are mixed together so as to produce a blend in which the fibres are intimately mixed so that there is a uniform distribution of the different fibres incorporated in the mix. The more uniform the distribution that is required, the greater the amount of blending that needs to be done by means of, for example, carding, so that uniformity can be guaranteed.

A particular problem arises with fibre blends for use in tampons. Because each tampon uses only about 2 g of fibre, and each tampon has to have a consistent level of absorbency, to comply with absorbency labelling regulations such as those of the US Federal Drug Administration, a very intimate blend of fibres is required to ensure consistency of the absorbency between each 2 g portion of blended fibres. Since each 2 g portion undergoes no further blending once it is formed into a tampon, each portion must contain as near as possible the same ratio of shaped to irregular fibres for consistency of absorbency from one tampon to the next.

The present invention provides a method of forming a tampon having a blend of fibres so that the eventual product can have a predetermined absorbency, whilst reducing and possibly removing the need to go through the time consuming and, therefore, expensive selecting, opening and carding routines. This means that, by use of the present invention, tampons with tailored absorbency can be produced on demand.

SUMMARY OF THE INVENTION

By the present invention there is provided in a method for the production of a tampon formed of a blend of regenerated solid cellulosic viscose fibres, said blend including a first set of fibres having a first cross-sectional characteristic and a second set of fibres having a second cross-sectional characteristic, said first cross-sectional characteristic being different to said second cross-sectional characteristic, the improvement which comprises forming said blend by forming a tow of viscose rayon fibres having the same blend ratio of first and second sets of fibres as in said tampon by spinning viscose dope through jet means to form a plurality of filaments, the jet means having a plurality of dimensionally controlled holes pierced therein, whereby the plurality of different fibre cross-sectional shapes or sizes are simultaneously formed directly in the tow by spinning the viscose dope through the jet means having the required plurality of different shaped or sized holes pierced therein.

The tow may be cut to form staple fibre, and is preferably cut prior to drying.

There may be a plurality of individual spinnerette plates, each plate having pierced holes of the same cross-sectional shape at their exit, and the cross-sectional shape of the pierced holes differing between the plates. The individual spinnerette plates may be in the form of inserts, mounted in an insert holder. The inserts may be shaped as thimbles. Such jets in the form of a plate containing a plurality of individual thimbles are herein (and commonly) referred to as a cluster jet.

The pierced holes in a single spinnerette plate may have differing cross-sectional shapes, preferably the plate may have a plurality of segments each segment containing holes of the same shape but different to the shape of the holes in at least one other segment.

Some at least of the pierced holes may be circular or triangular in cross-sectional shape. Some of the pierced holes may be multi-limbed in shape. The multi-limbed pierced holes may be Y-shaped, and are preferably as described in EP-B-0301874.

It is possible to produce a blend of fibres as required for making a tampon in accordance with the invention by either spinning from a single spinnerette having a variety of different shaped orifices such as Y-shaped and conventional round orifices pierced in the spinnerette. Alternatively, it is possible to use a cluster jet with a plurality of thimbles, some of which have conventional circular holes and others of which have the shaped holes, particularly the holes as defined in EP-B-0301874. Further alternatively it is possible to produce a combined tow from a plurality of individual tows, each individual tow being of one type of cross-sectional fibre, with the different tows from different jets being of different cross-sectional size or shape.

There may be three or more different cross-sectional sizes or shapes of fibres.

The two or more sets of fibres may be substantially the same cross-sectional shape but of different decitex.

The advantage of producing fibre blends in this way, which can be referred to as "spun blending", is that it is possible to spin the actual mixture of fibres required, and then after cutting the fibre to form staple, to wash and dry the mixture. The fibres from different shaped or sized holes can, therefore, become thoroughly blended and intermingled during the cutting, washing and drying operation particularly if the fibre is cut wet, washed on beds (rather than being washed in tow form) and dried in the cut condition. If the fibre is dried on a flat bed dryer with turn-over, then this will further aid the blending of the different individual filaments. The product emerging, therefore, is in effect spun blended i.e. is an instantly available blend without the need for any significant further processing, unless that is required for some reason.

In a particularly preferred form of the invention, the fibre is produced by spinning viscose dope through a plurality of separate spinnerettes each in the form of a thimble with each respective spinnerette having holes of a single shape only, some of the spinneretres having Y-shaped holes and some having circular holes. Such cluster jets are mounted in a holder. This means that by removing the cluster jets from the holder and varying the ratio of thimbles with round holes to those with Y-shaped holes it is a simple matter to alter the ratio of shaped to irregular fibres in the blend and thus in the tampons produced therefrom. Alternatively, a single spinnerette plate with segments of holes of different shape can be used. The process for making the fibre is otherwise perfectly conventional and the shaped fibres are, as set out above, formed in accordance with the teachings of EP-B0301874.

The advantage of the invention is, therefore, that blended fibre for tampon production can be produced having tailored properties. By varying the ratio of Y-shaped holes, or other specifically non-circular shaped holes, to circular holes in the one or more spinnerette plate(s), the absorbency characteristics of the spun blend fibre can be tailored to those characteristics desired in the final tampon, within the range of almost 100% circular to almost 100% non-circular shaped pierced holes.

For purposes of regularity, it is necessary to form shaped holes in the spinnerette plate(s) by a piercing process. Any desired piercing process may be used, the holes may be formed by drilling, spark erosion or punching or a combination of these or by any other suitable method. The or each spinnerette plate can be formed of any suitable sheet metal material, such as a precious metal alloy.

Preferably one of the sets of filaments are multi-limbed filaments, each filament being a solid filament of regenerated cellulosic material having a decitex of less than 5.0 and a multi-limbed cross-section, each limb having a length-to-width aspect ratio of at least 2:1.

The length-to-width aspect ratio of the filament limbs of that set is generally from 2:1 to 10:1, preferably from 2:1 to 7:1, and more preferably from 3:1 to 5:1. In general, the higher the aspect ratio, the higher the degree of free volume of the filaments. This gives a high degree of absorbency when the filaments are in staple fibre form, provided that the limbs are not so long and thin that they bend back upon themselves.

The filament of one set of fibres according to the invention preferably has 3 or 4 limbs, although it may have more than 4 limbs if desired, and also preferably has a cross-sectional shape that is generally (i.e. largely) symmetrical about at least one axis, as in a Y-, X-, H- or T- shaped filament cross-section, although other shapes are possible. Preferably, the filament has a Y-shaped cross-section. The angle between the limbs varies according to the cross-sectional shape and can be, for example, from 5° to 180°, although, it is preferred that the filament cross-section is as regular as possible.

As mentioned above, the filament according to the invention has a low decitex of less than 5.0, a low decitex being advantageous for high absorbency products. Generally the decitex is between 0.5 and 5.0, but more preferably is between 1.5 and 4.0.

All of the viscose rayon filaments in a tampon produced according to the invention are advantageously produced in the form of staple fibre, and the invention further provides such staple fibre. The combination of the multi-limbed cross-sectional shape and the low decitex gives filaments which in staple fibre form exhibit a high absorbency. Usually the fibre having the limbs has a total free absorbency (TFA) of at least 24 grams of water per gram of the fibre using the test as set out in British Pharmacopoeia 1980. Standard Methods (BP 1980, SDM) XI.A, p.928. For instance, a TFA in the range up to 28 g/g can be obtained.

Preferably any multi-limbed filaments in the blend substantially all have substantially the same cross-sectional shape.

The filaments used in a method according to the invention are viscose, and are conveniently spun from a standard (normal) viscose composition using standard (normal) viscose spinning conditions, with the exception that for multi-limbed fibres, multi-limbed shaped extrusion holes in the spinnerette are substituted for the conventional circular shaped holes to produce one of the sets of fibres.

The viscose composition used for spinning the filaments of the invention may be a commonly used viscose, typically having a cellulose content of 5 to 12% by weight and a caustic soda content of 4 to 10%, preferably 5 to 7%, by weight. Filaments may be spun over the full range of salt figures, although viscose having a salt figure of 4.0 to 12.0 is generally used. The ball-fall viscosity of the viscose composition used can be from 15 to 180 seconds at 18° C., but is preferred to be from 45 to 55 seconds at that temperature.

The filaments of the one fibre set are preferably spun through extrusion holes having a multi-limbed shape similar to the desired shape of the filaments. Typically the spinnerette is made from a gold-platinum alloy and the extrusion holes are formed by conventional methods such as spark erosion or mechanical punching. To achieve filament limb aspect ratios of at least 2:1 together with a filament decitex of less than 5.0 the dimensions of the limbs of the extrusion holes are preferably between 50 µm and 250 µm long and between 20 µm and 40 µm wide.

All of the filaments of both sets of fibre are spun into spin baths which can conveniently be of a standard spin bath composition for viscose spinning. Typically this composition includes (all by weight) from zero to 3%, preferably 0.5 to 2%, of zinc sulphate, 6 to 20%, preferably 7 to 10%, of sulphuric acid and 10 to 28%, preferably 20 to 26%, of sodium sulphate. The spin bath temperature is generally between 50 and 60° C., although higher and lower temperatures may be used.

Higher absorbencies can be achieved by adapting the process to give a slower rate of filament regeneration. The regeneration rate can be slowed down by altering one or more of the spinning conditions, for example by decreasing the acid level and/or increasing the sulphate level. Alternatively, or in addition, the viscose can be modified by a viscose modifier which is usually added to the viscose composition prior to spinning. Any of the commonly available viscose modifiers may be employed, examples being polyalcohols, soluble dithiocarbonates, soluble aliphatic and alicyclic amines, oxyethanols and quinoline. Polyglycols are preferred, especially PEG-1500 (polyethylene glycol where 1500 indicates the average molecular weight of the chain).

In general, tampons are manufactured in one of two forms; longitudinally expanding or radially expanding. For either type the absorbency of the tampon is linked to its stability, in that any modification made to the tampon fibre to increase its absorbency generally has the effect of decreasing its stability. A tampon formed from fibre according to the invention has the advantage that it can be manufactured to have an acceptance stability together with high absorbency and great uniformity.

The invention is distinguished from the random products which would be produced using the porous extrusion media described in U.S. Pat. No. 3670069, where no control over the shape of the product is possible, and hence no control over the properties of the material is possible.

BRIEF DESCRIPTION OF THE DRAWINGS

By way of example, embodiments of the present invention will now be described with reference to the accompanying drawings of which:

FIG. 1 is a schematic perspective view of a viscose staple production plant, used to produce tampons, FIG. 2 is a sectional view of a single jet for use in the plant of FIG. 1, FIG. 3 is a view in the direction of arrow III of FIG. 2 of a single spinnerette.

DESCRIPTION OF PREFERRED EMBODIMENTS

Figure 4:
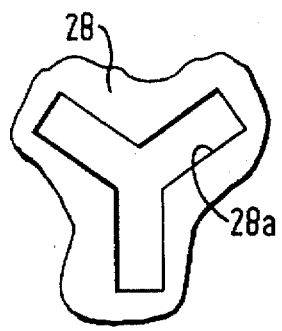
FIGS. 4 and 5 are enlarged scrap views of Y-shaped and circular holes for a spinnerette of FIG. 3.

The production of conventional rayon staple fibre is well known. It involves the formation of a viscose spinning solution, often referred to as a viscose dope by dissolving cellulose xanthate in dilute sodium hydroxide solution, and after ripening, filtering the solution before pumping the viscose dope under pressure through a plurality of spinneretres into a spin bath.

Similarly, the production of tampons is also a well know technique. Essentially the tampon is formed in any suitable manner from a plurality of fibres, normally in staple form although there have been proposals to manufacture tampons from continuous tows of fibre. The properties of the tampon thus formed are in part dependent on the nature and properties of the fibres from which the tampon is manufactured. It is a feature of the present invention that the improved tampon can be formed in any suitable manner using the preblended material knowing that each tampon will have an almost identical blend ratio of the different fibre types even at the very low weights of fibre present in any individual tampon. There will, therefore, be further description of the manufacture of the blended material, which can then be used in any form of tampon as desired.

Referring to FIG. 1 dope is shown schematically being passed through line 1 into a filter 2 and from the filter, via line 3 and pump 4, into a distributor 5.

From the distributor 5, a series of rounder arms 6 lead the dope to a jet means in the form of a series of spinneretres 7 located in a regeneration or spin bath 8 below the level of liquor in the spin bath. The spinneretres are described in more detail below. On emerging from the spinneretres 7 the viscose dope comes into contact with the strongly acidic regeneration bath, and the acid in the bath reacts with the outer molecules of cellulose xanthate, liberating $CS_2$ and regenerating cellulose in the form of an outer skin or cuticle. Further reaction between the contents of the bath and the filament result in a regeneration of cellulose filaments within the bath. These filaments (shown at 9) pass over a roller or godet 10 and then into a cutter 11. In the cutter 11 the continuous filaments of viscose rayon are cut to form staple fibre 12. The staple fibre 12 falls from the cutter 11 onto a moving endless belt 13. The staple fibre 12 is then washed and passed via a suitable delivery system 14 onto a porous endless belt 15 which passes through a heated drying chamber 16. The staple fibre is overturned by a toothed belt system 17 and redeposited onto a further porous endless belt 18. The dry fibre then emerges at 19 from the drying chamber 16 is picked off at 20 and is baled as at 21. A tampon produced by conventional means from the bales of fibre is shown at 32.

Normally all of the spinneretres 7 would be identical in design. Each spinnerette effectively comprises a thin sheet, typically of precious metal, formed with pierced apertures. The apertures are conventionally round and are formed by punching or drilling or a combination of both. Typically each spinnerette would have up to 50,000 holes and the fibre it creates is commonly referred to as an end. A number of ends are joined together to form the bundle of filaments or tow shown at 10A as it enters the cutter 11.

With the process of the invention, either each spinnerette 7 could have a series of different shaped holes or each spinnerette 7 could have the same shaped holes, but one spinnerette could have Y-shaped holes and the remaining spinnerette or spinnerettes could have conventional circular holes. Of course, up to N–1 of the spinnerettes could have Y-shaped holes where N is the total number of spinnerettes.

One form of spinnerette 7 is shown in cross-section in FIG. 2. The spinnerette comprises an enlarged head portion 22 forming a plenum or chamber 23 at the end of an outlet portion 24 of one gooseneck 6. An outer flange 25 is provided with a threaded portion 26. A spinnerette plate, generally indicated by 27, has a central domed portion 28 and a peripheral flange portion 29. The flange portion 29 is secured to the flange 25 by means of a large external annular nut 30.

Figure 5:
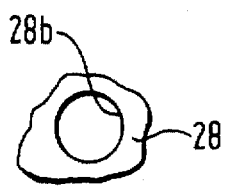

FIG. 3 is a view along the line of arrow III in FIG. 2 and shows the spinnerette plate 27. The central portion 28 can be seen to be surrounded by the flange portion 29. Pierced through the central portion 28 is a series of holes arranged in segmental patterns 29a to 29f. By arranging the holes in this pattern, the strength and mechanical integrity of the spinnerette plate is maintained and acid in the regeneration bath 8 is able to obtain access to the centre portion of the large number of filaments created on the emerging of dope from the spinnerette 7. Typically such a spinnerette could have up to 20,000 holes in the segments 29a to 29f. The spinnerette plate 27 can be formed of any suitable material such as a platinum/gold/rhodium alloy. The holes in each of the segments 29a to 29f can be the same shape, or alternatively the holes in one segment could be Y-shaped as illustrated at 28a in FIG. 4 whilst the holes in the other segments could be conventional circular holes as illustrated at 28b in FIG. 5. Alternatively, all of the holes in a single spinnerette plate 27 could be of Y-shaped or circular form, with different spinnerette plates in the overall spinning plant being formed with Y-shaped or circular holes to produce the spun blended viscose.

In the case of a spinnerette in which one or more of the segments 29a to 29f has non-circular shaped holes, with the remaining holes being circular, the tow emerging from the spinnerette would itself be a mixed tow. In the case where each spinnerette has holes all of the same shape, in a plant having a multiplicity of spinnerettes, then the tow would only be formed of multiple shaped fibres when the individual tows from each spinnerette were combined to form a combined tow.

In an alternative form of spinnerette as illustrated in FIGS. 6 to 9, the spinnerette is formed as a cluster jet.

Cluster jets are in themselves well known. A cluster jet comprises a holder, usually of metal such as HASTALOY (™) or stainless steel pierced with a number of through bores, commonly partially recessed, in which are located a number of inserts, commonly referred to as thimbles.

Figure 6:
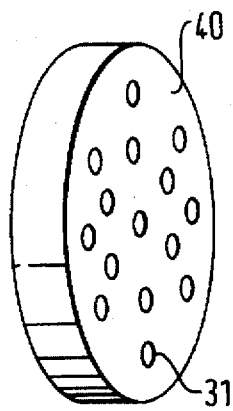
FIG. 6 is a schematic perspective view of a plate of a cluster jet.
Figure 7:
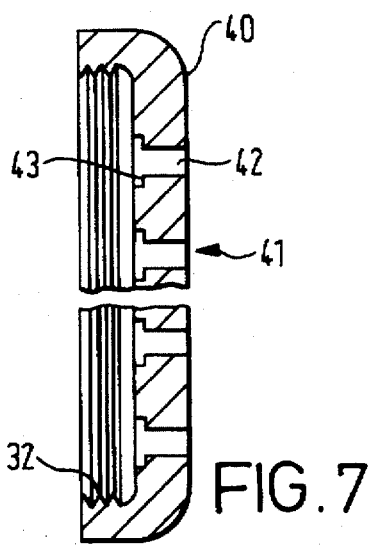
FIG. 7 is a sectional view of parts of the plate of FIG. 6.
Figure 8:
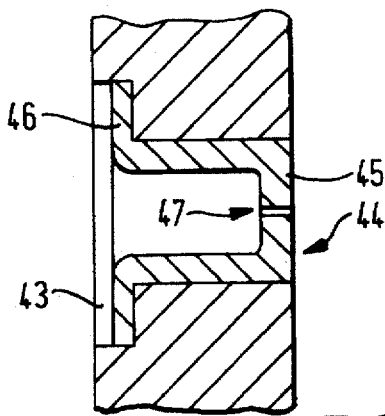
FIG. 8 is an enlarged view of a portion of FIG. 7.
Figure 9:
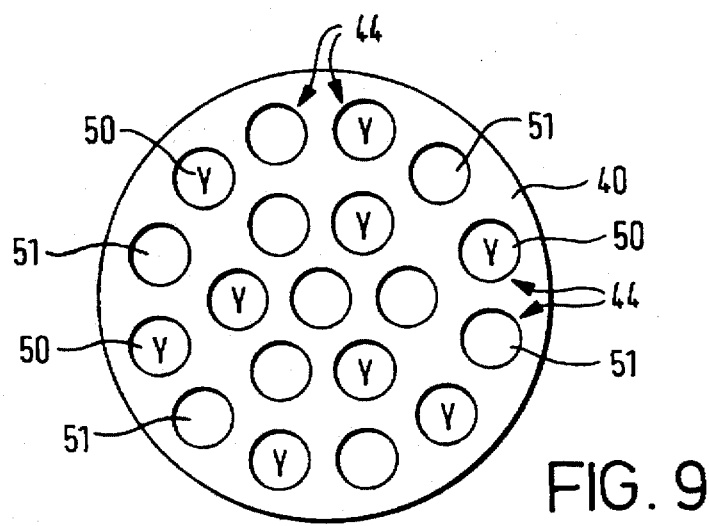
FIG. 9 is a view of the plate of a cluster jet having thimbles containing either circular or Y-shaped holes.

Such a cluster jet is schematically shown in a general perspective view in FIG. 6. The cluster jet comprises a HASTALOY disc 40 formed with a series of bores such as 31 in which are located the individual thimbles. FIG. 7, which is a schematic cross-section of a cluster jet holder, shows that the disc 40 is provided with an internal threaded portion 32 so that it can be screwed onto the screwed portion 26 of the flange 25 of the end of the gooseneck as illustrated in FIG. 2. Thus the disc 40 replaces both the nut 30 and the spinnerette plate 27.

Formed in the disc 40 are a series of bores 41 which have a central cylindrical portion 42 and a stepped inlet portion 43. Located in each bore 41 is a thimble such as the thimble 44. This thimble forms an insert and has a domed central region generally indicated by 45 and an outwardly directed flange portion 46 which is located in the inlet portion 43. The thimbles or inserts 44 are formed with a plurality of holes such as 47 through which the viscose dope passes during the spinning process. Typically each thimble could have 200 to 2,000 holes, depending on the size and complexity of the hole shape. The thimbles would conventionally be formed of a precious metal such as a platinum/gold/rhodium alloy.

In an individual cluster jet, one or more of the thimbles 44 in the disc 40 could be formed with Y-shaped holes, such as the as the thimbles 50 (FIG. 9) and the remaining thimbles 51 could be formed with conventional circular holes. This means that the end of fibres emerging from an individual cluster jet has an intimate mixture of non-circular shaped and conventional fibres. If such ends are brought together to form a combined tow, again the amount of intimate mixing is very high even before the process of cutting the filaments to form staple fibre and subsequently sluicing the fibre onto a washing belt. During the washing, drying and other subsequent operations, the fibres become even further intermingled to produce a very well blended product, requiring a minimum if any of subsequent blending, particularly for use in the production of tampons 32.

The tampons produced by the process of the present invention can be optimised in a number of different ways.

Firstly, different cross-sectional shapes of fibre have different optimum decitexes when used in tampons of particular types. Thus it is currently believed that Y-shaped cross-sectional fibres for tampon usage have an optimum decitex at about 3.3. However, the "circular" or conventional shaped fibres of viscose rayon have an optimum decitex of about 2.4. Thus the blends produced in accordance with the present invention can have their optimum decitexes for the difference cross-sectional shapes of fibres. It will be appreciated that blending by conventional blending routes fibres of different decitexes is even harder than blending fibres of the same decitex.

Secondly, cellulosic fibres hold liquid both inside them and around them in the interstitial spaces between the fibres. When the fibres in a tampon are all of the same decitex, the interstitial spaces are all approximately the same. By forming a blend in accordance with the present invention, however, there is provided in the tampon a variety of interstitial spaces in terms of sizes and shapes, because of the different packing of the different types of fibres compared to the case where a tampon is made of all identical fibres. This variation in interstitial sizes and shapes affects the absorption capacity and the absorption characteristics in terms of time of the tampons. This means that the tampon manufacturer can tailor the absorption characteristics of the tampons produced in accordance with the present invention both in terms of absorption capacity and speed in a way not possible with tampons where all of the fibres are substantially identical.

We claim:

1. In a method for the production of a tampon, the method comprising forming said tampon from a blend of regenerated solid cellulosic viscose fibres, said blend including a blend ratio of a first set of fibres having a first cross-sectional characteristic and a second set of fibres having a second cross-sectional characteristic, said first cross-sectional characteristic being different from said second cross-sectional characteristic, the improvement which comprises forming said tampon of said blend produced by forming a tow of viscose rayon fibres having the same blend ratio of said first and second sets of fibres by spinning viscose dope through jet means having a plurality of dimensionally controlled, different shaped or sized holes pierced therein and forming a plurality of different fibre cross-sectional shapes or sizes simultaneously directly in the tow.

2. A method as claimed in claim 1 in which the jet means is a cluster jet containing a plurality of thimbles, some of the thimbles having circular cross-section holes and some of the thimbles having non-circular cross-section holes.

3. A method as claimed in claim 2 in which at least some of the non-circular cross-section holes are Y-shaped.

4. A method as claimed in claim 1 in which the tow is cut into staple when wet and washed and dried as staple fibre.

5. A method as claimed in claim 2 in which the tow is cut into staple when wet and washed and dried as staple fibre.

6. A method as claimed in claim 3 in which the tow is cut into staple when wet and washed and dried as staple fibre.

7. A method as claimed in claim 3 in which the Y-shaped fibres have a decitex in the range 0.5 to 5 and each limb of each Y-shaped fibre has an aspect ratio in the range 2:1 to 10:1.

8. A method as claimed in claim 7 in which the decitex of each Y-shaped fibre is in the range 1 to 3 and in which the aspect ratio of each limb is in the range 3 to 7.

9. A method as claimed in claim 3 in which the cross-sectional shape of all of the Y-shaped fibres is substantially the same.

10. A method as claimed in claim 6 in which the cross-sectional shape of all of the Y-shaped fibres is substantially the same.

11. A method as claimed in claim 7 in which the cross-sectional shape of all of the Y-shaped fibres is substantially the same.

12. A method as claimed in claim 8 in which the cross-sectional shape of all of the Y-shaped fibres is substantially the same.

13. A method of producing a tampon from a tow of viscose rayon fibres, the tow containing fibres having at least two different cross-sectional shapes and the proportions of fibres of any given cross-sectional shape in the complete tow being pre-determined, said method comprising the steps of:

(a) directly producing the required pre-determined proportions of filaments of said different cross-sectional shapes by spinning a viscose dope through jet means having holes of the required numbers of each required cross-sectional shape, (b) forming said tow from said filaments, (c) cutting said tow into a plurality of staple filaments and (d) forming the tampon from said staple filaments.

* * * * *